United States Patent
Ishii et al.

(10) Patent No.: US 8,217,196 B2
(45) Date of Patent: Jul. 10, 2012

(54) PROCESS FOR PRODUCING α-FLUORO-β-AMINO ACIDS

(75) Inventors: Akihiro Ishii, Kawagoe (JP); Takako Yamazaki, Kawagoe (JP); Manabu Yasumoto, Kawagoe (JP); Takashi Masuda, Kawagoe (JP); Hideyuki Tsuruta, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 158 days.

(21) Appl. No.: 12/919,108

(22) PCT Filed: Apr. 21, 2009

(86) PCT No.: PCT/JP2009/057897
§ 371 (c)(1), (2), (4) Date: Aug. 24, 2010

(87) PCT Pub. No.: WO2009/133789
PCT Pub. Date: Nov. 5, 2009

(65) Prior Publication Data
US 2011/0015428 A1 Jan. 20, 2011

(30) Foreign Application Priority Data

Apr. 28, 2008 (JP) ................................. 2008-117481
Apr. 20, 2009 (JP) ................................. 2009-101506

(51) Int. Cl.
*C07C 227/16* (2006.01)
(52) U.S. Cl. ........................................................ 560/172
(58) Field of Classification Search .......................... None
See application file for complete search history.

(56) References Cited

U.S. PATENT DOCUMENTS

2008/0125589 A1 5/2008 Ishii et al.
2010/0087673 A1 4/2010 Ishii et al.

FOREIGN PATENT DOCUMENTS

| JP | 2008-201770 A | 9/2008 |
| WO | WO 2006/038872 A1 | 4/2006 |
| WO | WO 2006/098444 A1 | 9/2006 |
| WO | WO 2008/122611 A1 | 10/2008 |

OTHER PUBLICATIONS

David F. Hook et al., "Probing the Proteolytic Satability of Beta-Peptides Containing Alpha-Fluoro and Alpha-Hydroxy-Beta-Amino Acids", ChemBioChem, 2004, vol. 5, No. 5, p. 697-706.
International Search Report with English translation dated Jun. 2, 2009 (Five (5) pages).
PCT/ISA/237 (Three (3) pages).
Journal of American Chemical Society (U.S.), 1982, vol. 104, p. 5836-5837.
John Wiley & Sons, Inc, "Protective Groups in Organic Synthesis", Third Edition, 1999, (Twenty-six (26) pages).
Jikken Kagaku Koza 22, 4th Edition, Organic Synthesis IV: -Acid, Amino acid, Peptide-, (edited by the Chemical Society of Japan, published by MARUZEN Co. Ltd., Heisei 4, p. 214-228, 1992.
David F. Hook et al., "Probing the Proteolytic Satability of Beta-Peptides Containing Alpha-Fluoro and AlphaHydroxy-Beta-Amino Acids", ChemBioChem, 2004, vol. 5, No. 5, p. 697-706.
J. Kollonitsch et al., "Fluorodehydroxylation, a Novel Method for Synthesis of Fluoroamines and Fluoroamino Acids", J. Org. Chem., 1979, vol. 44, No. 5, p. 771-777.
Franklin A. Davis et al., "Sythesis of (2R, 3S)-Methyl-2-fluoro-3-(N-benzoylamino)-3-phenylpropanoate: Modified Side Chain of Taxol", Tetrahedron: Asymmetry, 1994, vol. 5, No. 6, p. 955-960.

*Primary Examiner* — Kamal Saeed
(74) *Attorney, Agent, or Firm* — Crowell & Moring LLP

(57) ABSTRACT

By reacting a β-hydroxy-α-amino acid with sulfuryl fluoride ($SO_2F_2$) in the presence of an organic base, it is possible to produce an α-fluoro-β-amino acid of the formula [2].

[Chem. 44]

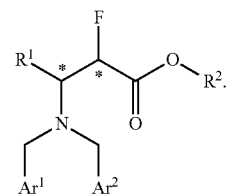

[2]

By using a C8-12 tertiary amine having two or more alkyl groups of C3 or higher, and especially diisopropylethylamine, as the organic base, by-production of quantery ammonium salts is effectively suppressed. By applying the production process of the present invention, it is possible to very easily produce (2R)-3-(dibenzylamino)-2-fluoropropionic acid methyl ester, which is extremely important as a pharmaceutical intermediate, with high positional selectivity even on an industrial scale.

3 Claims, No Drawings

PROCESS FOR PRODUCING α-FLUORO-β-AMINO ACIDS

TECHNICAL FIELD

The present invention relates to an industrial production process of α-fluoro-β-amino acids, which are important as intermediates of pharmaceutical and agrichemical products.

BACKGROUND ART

An α-fluoro-β-amino acid, which is the target of the present invention, is an important intermediate of pharmaceutical and agrichemical products. As a conventional production process of an α-fluoro-β-amino acid, there has been reported dehydroxyfluorination of a β-hydroxy-α-amino acid, accompanied by 1,2-rearrangement, with the use of DAST (cf. Scheme 1: Non-Patent Document 1).

Scheme 1

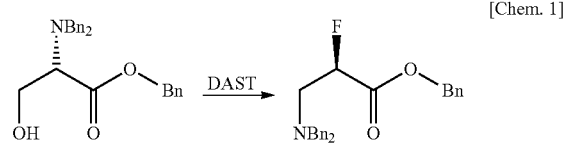

[Chem. 1]

Bn: benzyl, DAST: $(CH_3CH_2)_2NSF_3$

There has also been disclosed an example in which a similar reaction is performed in two steps (cf. Scheme 2: Patent Document 1).

Scheme 2

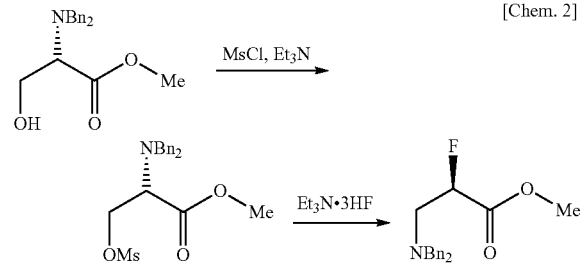

[Chem. 2]

Bn: benzyl, Me: methyl, Ms: methanesulfonyl, Et: ethyl

Further, the present applicant has disclosed dehydroxyfluorination of an alcohol with the combined use of sulfuryl fluoride ($SO_2F_2$) and an organic base (cf. Patent Document 2).

PRIOR ART DOCUMENTS

Patent Documents

Patent Document 1: International Publication No. 2006/038872

Patent Document 2: International Publication No. 2006/098444 (Japanese Laid-Open Patent Publication No. 2006-290870)

Non-Patent Document

Non-Patent Document 1: Journal of American Chemical Society (U.S.), 1982, Vol. 104, P. 5836-5837

DISCLOSURE OF THE INVENTION

It is an object of the present invention to provide an industrial production process of an α-fluoro-β-amino acid.

In Non-Patent Document 1, DAST is used as the dehydroxyfluorination agent. This reaction agent is limited to small-scale production applications because of being expensive and having a danger of explosion. It is thus required to adopt an alternative reaction agent suitable for large-scale production applications.

In Patent Document 1, the reaction is performed in two steps although the reaction agents used are suitable for large-scale production applications. This leads to complicated process operations including post treatment operation, whereby high productivity cannot be expected. Further, there occurs a considerable amount of a position isomer (β-F form) that has a fluorine atom substituted on a carbon atom thereof to which a hydroxyl group is covalent bonded, as a by-product other than the target 1,2-rearrangement product (α-F form), as disclosed in Patent Document 1 (α-F form:β-F form=15 to 20:1). (In particular, Example 1 (Step 3) of Patent Document 1 clearly indicates that the crude product contains 5% of such a position isomer.) It cannot always be said that the position selectivity of the reaction is satisfactory for use of the target product as a pharmaceutical intermediate. This results in a burden on the purification of the position isomer of similar properties.

Moreover, it has been completely unknown whether the disclosed dehydroxyfluorination reaction conditions of Patent Document 2 can suitably be adopted for the target reaction of the present invention, i.e., the dehydroxyfluorination of a β-hydroxy-α-amino acid accompanied by 1,2-rearrangement.

Therefore, there has been a strong demand to develop a process for producing an α-fluoro-β-amino acid industrially with high position selectivity.

As a result of extensive researches made in view of the above problems, the present inventors have newly found that it is possible to produce an α-fluoro-β-amino acid of the general formula [2] by reaction of a β-hydroxy-α-amino acid of the general formula [1] with sulfuryl fluoride in the presence of an organic base. The present inventors have also found that this reaction can suitably be applied for production of the α-fluoro-β-amino acid in not only a racemic form but also an optically active form, namely, the α-fluoro-β-amino acid of the general formula [2] can be obtained with high optical purity by the use of the β-hydroxy-α-amino acid of the general formula [1] in an optically active form (high optical purity).

The present inventors have further newly found that the 1,2-rearrangement product can be obtained with high position selectivity when the β-position of the starting substrate is unsubstituted. In particular, the starting substrate in which both of $Ar^1$ and $Ar^2$ are phenyl; and $R^2$ is methyl, ethyl or benzyl can be easily available or prepared on a large scale; and the resulting fluorinated product can easily undergo a conversion reaction such as deprotection (e.g. conversion from —$N(CH_2Ph)_2$ to —$NH_2$, conversion from —$CO_2R^3$ to —$CO_2H$, conversion from the optically active α-fluoro-β-amino acid to optically active 2-fluoro-3-amino propanol (which can be a synthon of optically active 2-fluoro-3-substituted propylamine particularly important as a pharmaceutical/agrichemical intermediate) etc.). An optically active β-hydroxy-α-amino acid of the general formula [3] is thus preferred as the starting substrate of the present invention. The starting substrate of the present invention is more preferably an optically active β-hydroxy-α-amino acid of the formula [5], in view of the importance of the α-fluoro-β-amino acid as the pharmaceutical intermediate. More specifically, a N,N-dibenzyl derivative of L-serine methyl ester is in particular preferred.

Further, the organic base of the present invention is preferably a tertiary amine having a carbon number of 8 to 12 and containing two or more alkyl groups of 3 or more carbon atoms, more preferably diisopropylethylamine.

The following is a reaction example in which a N,N-dibenzyl derivative of L-serine methyl ester, particularly suitable as the starting substrate of the present invention, undergoes dehydroxyfluorination accompanied by 1,2-rearrangement with the use of triethylamine as the organic base (cf. Scheme 3, Example 2). In the present invention, the dehydroxyfluorination accompanied by 1,2-rearrangement proceeds through intramolecular ring-closure of a fluorosulfuric ester derivative of the starting substrate to an aziridinium intermediate and ring-opening fluorination of the aziridinium intermediate with inversion of the stereochemistry at the α-position to thereby produce the target 1,2-rearrangement product. It has been newly found that, in the case of using as the organic base triethylamine (of carbon number 6) for which so much steric effect cannot be expected, the triethylamine is partially involved in the intramolecular ring-closure of the fluorosulfuric ester to the aziridinium intermediate and the ring-opening fluorination of the aziridinium intermediate to the target product so that there occur quaternary ammonium salts (corresponding to β-form and α-form, respectively) as by-products.

Scheme 3

[Chem. 3]

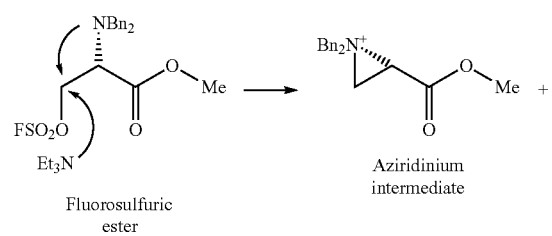

Fluorosulfuric ester

Aziridinium intermediate

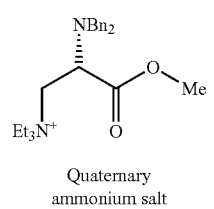

Quaternary ammonium salt (β-form)

(Fluorosulfuric anion omitted)

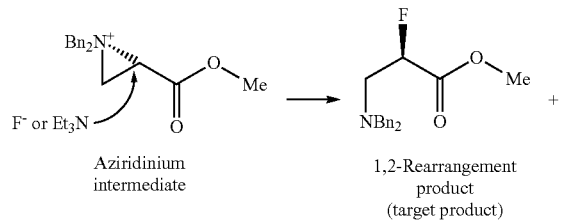

Aziridinium intermediate 1,2-Rearrangement product (target product)

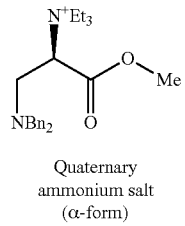

Quaternary ammonium salt (α-form)

Et: ethyl, Bn: benzyl, Me: methyl

Under these circumstances, the present inventors have focused attention on the steric effect of the organic base and have newly found that the use of the "tertiary amine having a carbon number of 8 to 12 and containing two or more alkyl groups of 3 or more carbon atoms" as the organic base makes it possible to effectively prevent by-production of the quaternary ammonium salt during the dehydroxyfluorination accompanied by 1,2-rearrangement. The desired steric effect of the tertiary amine can be obtained sufficiently when the tertiary amine has a carbon number of 8 or more and contains two or more alkyl groups of 3 or more carbon atoms. The carbon number of the tertiary amine is thus preferably up to 12 in view of the large-scale availability of the amine, the productivity of the reaction system and the like. It is particularly preferable to use diisopropylethylamine.

As described above, the present inventors have found the particularly useful techniques for industrial production of the α-fluoro-β-amino acid. The present invention is based on these findings.

Namely, there is provided according to the present invention a process (first process) for producing an α-fluoro-β-amino acid of the general formula [2], comprising reacting a β-hydroxy-α-amino acid of the general formula [1] with sulfuryl fluoride ($SO_2F_2$) in the presence of an organic base

[Chem. 4]

[Chem. 5]

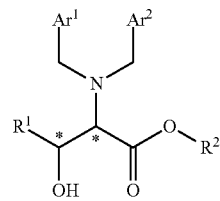

where $R^1$ represents a hydrogen atom, an alkyl group or an aromatic ring group; $R^2$ represents an alkyl group; $Ar^1$ and $Ar^2$ each independently represent an aromatic ring group; * represents an asymmetric carbon (when $R^1$ is a hydrogen atom, the β-position carbon atom is not an asymmetric carbon); the alkyl group or aromatic ring group represented by $R^1$, $R^2$, $Ar^1$ and $Ar^2$ may have a substituent on any of carbon atoms thereof; and the aromatic ring group may be an aromatic heterocyclic ring group containing a hetero atom.

The first process may be a process (second process) for producing an optically active α-fluoro-β-amino acid of the general formula [4], comprising reacting an optically active β-hydroxy-α-amino acid of the general formula [3] with sulfuryl fluoride (SO$_2$F$_2$) in the presence of a tertiary amine having a carbon number of 8 to 12 and containing two or more alkyl groups of 3 or more carbon atoms

[Chem. 6]

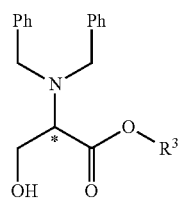

[3]

[Chem. 7]

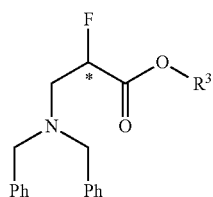

[4]

where R$^3$ represents a methyl group, an ethyl group or a benzyl group; Ph represents a phenyl group; and * represents an asymmetric carbon.

The first or second process may be a process (third process) for producing an optically active α-fluoro-β-amino acid of the general formula [6], comprising: reacting an optically active β-hydroxy-α-amino acid of the formula [5] with sulfuryl fluoride (SO$_2$F$_2$) in the presence of diisopropylethylamine

[Chem. 8]

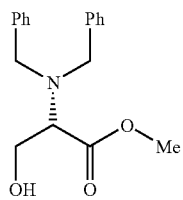

[5]

[Chem. 9]

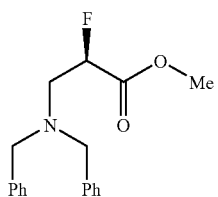

[6]

where Me represents a methyl group; and Ph represents a phenyl group.

DETAILED DESCRIPTION

The advantages of the present invention over the prior art technologies will be described below.

The present invention is advantageous over Non-Patent Document 1, in that the reaction can be performed with a dehydroxyfluorination agent that is suitable even for large-scale production applications. Sulfuryl fluoride used in the present invention has widely been utilized as a fumigant and can be industrially available at low cost without a danger of explosion.

The present invention is advantageous over Patent Document 1, in that the reaction (a series of fluorosulfuric esterification of the starting substrate, intramolecular ring-closure of the fluorosulfuric ester to an aziridinium intermediate and ring-opening fluorination of the aziridinium intermediate) can be performed in one step with very high productivity and is thus suitable for large-scale production applications.

Furthermore, a "salt or complex of the organic base and hydrogen fluoride" stoichiometrically generated as a by-product of the fluorosulfuric esterification effectively serves as a fluorine source (fluorine anion (F$^-$)) in the ring-opening fluorination of the aziridinium intermediate in the present invention. There is thus no need in the present invention to newly add a fluorine source such as "triethylamine tris(hydrogen fluoride) complex" used in Example 1 (Step 3) of Patent Document 1.

In Example 1 of Patent Document 1, a chlorine anion (Cl$^-$) is generated stoichiometrically as a by-product of the mesylation of Step 2. This chlorine anion has higher nucleophilicity than that of the fluorine anion so that, when the chorine anion enters into the reaction system of the fluorination of Step 3, the reaction of the chlorine anion and the aziridinium intermediate occurs preferentially to the reaction of the fluorine anion and the aziridinium intermediate and thereby generates a corresponding chloride as an impurity by-product (cf. Example 2 of Patent Document 1). It is necessary to completely remove the chlorine anion by-product by washing with water as a post treatment operation of the mesylation step. This however raises a need for water content control to perform the subsequent fluorination step efficiently and causes complication of the process operations. In the present invention, by contrast, no chlorine anion is generated as a by-product. There is thus no possibility of generating a chloride as an impurity by-product. There is also no need to perform the post treatment operation of Step 2 (Example 1 of Patent Document 1) as the reaction proceeds continuously.

The newly found reaction of the present invention, i.e., the dehydroxyfluorination accompanied by 1,2-rearrangement proceeds favorably even under very moderate reaction conditions so that the target 1,2-rearrangement product (α-F form) can be obtained with much higher position selectivity than in Patent Document 1 and Non-Patent Document 1. It has been verified by a comparison experiment using various conventional dehydroxyfluorination agents against the same starting substrate that the target α-F form can be obtained with higher position selectivity in the present invention regardless of the presence or absence of a substituent group at the β-position (cf. Scheme 4 (no substituent at the β-position): Example 1 and Comparative Example 1, Scheme 5 (methyl substituent at the β-position): Example 3 and Comparative Example 2: the relative position selectivity of various dehydroxyfluorination agents against the same substrate will be herein discussed in view of the fact that the starting substrate substituted by a methyl group at the β-position is basically likely to provide a β-F form.) The production process of the present invention has less burden on the purification of the position isomer of similar properties and is thus particularly suitable for production of the pharmaceutical intermediate for which high quality is required.

Scheme 4

[Chem. 10]

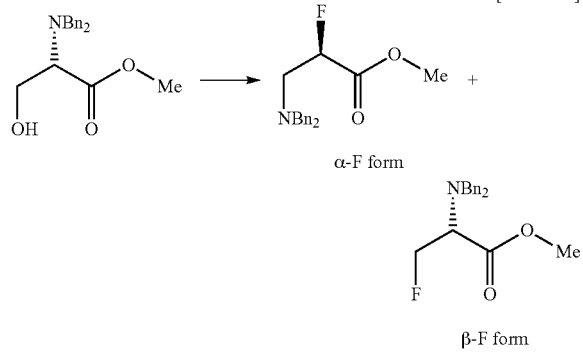

Example 1

SO$_2$F$_2$/i-Pr$_2$NEt α-F form:β-F form=98.5:1.5

Comparative Example 1

Follow-Up Experiment of Patent Document 1

1) MsCl/Et$_3$N, 2) Et$_3$N.3HF α-F form:β-F form=92.0:8.0
Bn: benzyl, Me: methyl, i-Pr: isopropyl,
Et: ethyl, Ms: methanesulfonyl

Scheme 5

[Chem. 11]

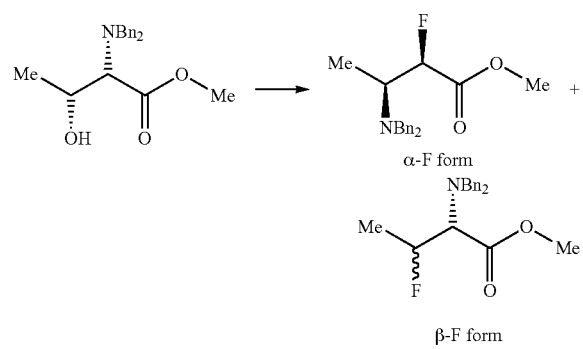

Example 3

SO$_2$F$_2$/i-Pr$_2$NEt α-F form:β-F form=71:29*[1, 2]

Comparative Example 2

DAST α-F form:β-F form=56:44*[1, 3]
Me: methyl, Bn: benzyl, i-Pr: isopropyl,
Et: ethyl, DAST: (CH$_3$CH$_2$)$_2$NSF$_3$
*[1]: β-F form as a total mixture of syn-isomer (the bottom side of the page) and anti-isomer (the top side of the page)
*[2]: syn-isomer: anti-isomer=69:31
*[3]: mostly syn-isomer (trace anti-isomer)

Further, it has been newly found that the dehydroxyfluorination reaction conditions of Patent Document 2 can suitably be adopted for the target reaction of the present invention, i.e., the dehydroxyflorination of the βhydroxy-α-amino acid accompanied by 1,2-rearrangement. The target product of Patent Document 2 (i.e., the product having a fluorine atom substituted on its carbon atom to which a hydroxyl group is covalent bonded; β-F form) is generated even in the present invention. However, when the βhydroxy-α-amino acid is used as the starting substrate in the present invention, the 1,2-rearrangement product (α-F form) is preferentially generated with high position selectivity; and the target product of Patent Document 2 (β-F form) is obtained as a minor product.

In the present invention, the target product can be obtained with high chemical purity and high yield without almost no difficult-to-separate impurity by-product. In addition, the inversion of the stereochemistry at the α-position proceeds with very high stereoselectivity. The target product can be obtained with high optical purity, through such inversion of the stereochemistry at the α-position, by using the starting substrate having high optical purity at the α-position.

Accordingly, the production process of the present invention is industrially readily practicable and can solve all of the above-mentioned prior art problems. The 1,2-rearrangement product can be obtained with higher position selectivity by the present invention than by the prior art technologies.

A production process of an α-fluoro-β-amino acid according to the present invention will be described in detail below.

In the present invention, an α-fluoro-β-amino acid of the general formula [2] is produced by reaction of a βhydroxy-α-amino acid of the general formula [1] with sulfuryl fluoride in the presence of an organic base.

In the β-hydroxy-α-amino acid of the general formula [1], $R^1$ represents a hydrogen atom, an alkyl group or an aromatic ring group.

As the alkyl group, there can be used those having 1 to 18 carbon atoms and having a linear structure, a branched structure or a cyclic structure (in the case of 3 carbons or more).

As the aromatic ring group, there can be used those having 1 to 18 carbon atoms, including aromatic hydrocarbon groups such as phenyl, naphthyl, anthryl etc. and aromatic heterocyclic groups containing nitrogen, oxygen or sulfur heteroatoms, such as pyrrolyl, furyl, thienyl, indolyl, benzofuryl, benzothienyl etc.

The alkyl group or aromatic ring group may have any number of and any combination of substituents on any of carbon atoms thereof. Examples of the substituents are: halogen atoms such as fluorine, chlorine, bromine and iodine; azide group; nitro group; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; lower alkylamino groups such as dimethylamino, diethylamino and dipropylamino; lower alkylthio groups such as methylthio, ethylthio and propylthio; cyano group; lower alkoxycarbonyl groups such as methoxycarbonyl, ethoxycarbonyl and propoxycarbonyl; aminocarbonyl (CONH$_2$); lower aminocarbonyl groups such as dimethylaminocarbonyl, diethylaminocarbonyl and dipropylaminocarbonyl; unsaturated groups such as alkenyl and alkynyl; aromatic ring groups such as phenyl, naphthyl, pyrrolyl, furyl and thienyl; aromatic ring oxy groups such as phenoxy, naphthoxy, pyrrolyloxy, furyloxy and thienyloxy; aliphatic heterocyclic groups such as piperidyl, piperidino and morpholinyl; protected hydroxyl groups; protected amino groups (including amino acids and peptide residues); protected thiol groups; protected aldehyde groups; protected carboxyl groups; and the like.

In the present specification, the following terms have the following meanings. The term "lower" means that the group to which the term is attached has a carbon number of 1 to 6 and has a linear structure, a branched structure or a cyclic structure (in the case of 3 carbons or more). It means that, when the "unsaturated group" is a double bond (alkenyl group), the double bond can be in a E-configuration, a Z-configuration or a mixture thereof. The "protected hydroxyl, amino (including amino acid or peptide residue), thiol, aldehyde and carboxyl groups" may be those having protecting groups described in "Protective Groups in Organic Synthesis", Third Edition, 1999, John Wiley & Sons, Inc. and the like. (Two or more functional groups may be protected with one protecting group.)

Further, the "unsaturated group", "aromatic ring group", "aromatic ring oxy group" and "aliphatic heterocyclic group" may be substituted with halogen atoms, azide group, nitro group, lower alkyl groups, lower haloalkyl groups, lower alkoxy groups, lower haloalkoxy groups, lower alkylamino groups, lower alkylthio groups, cyano group, lower alkoxycarbonyl groups, aminocarbonyl group, lower aminocarbonyl groups, protected hydroxyl groups, protected amino groups (including amino acids and peptide residues), protected thiol groups, protected aldehyde groups, protected carboxyl groups or the like.

Although the hydrogen atom, alkyl group or aromatic ring group is suitably used as $R^1$ in the β-hydroxy-α-amino acid of the general formula [1], $R^1$ is preferably a hydrogen atom or an alkyl group, more preferably a hydrogen atom. The β-hydroxy-α-amino acid of the general formula [1] in which $R^1$ is a hydrogen atom or a methyl group (alkyl group of 1 carbon atom) can be easily derived from serine or (allo)threonine. Similarly, the optically active β-hydroxy-α-amino acid can be easily derived from optically active serine or (allo)threonine without racemization. Each of the optically active serine and the (allo)threonine is commercially available in the form of L- and D-optical isomers. In particular, L-serine is industrially available at relatively low cost and is thus preferred as the raw substrate material of the present invention in view of the usability of the fluorinated product.

In the β-hydroxy-α-amino acid of the general formula [1], $R^2$ represents an alkyl group. Examples of the alkyl group as $R^2$ are the same as $R^1$ in the β-hydroxy-α-amino acid of the general formula [1]. This alkyl group may have a substituent on any of carbon atoms thereof. For example, the alkyl group may have one or more aromatic ring substituents. Among others, methyl, ethyl and benzyl are preferred as the alkyl group. Particularly preferred is methyl. The β-hydroxy-α-amino acid of the general formula [1] in which $R^2$ is methyl, ethyl or benzyl can be easily derived from a corresponding carboxylic acid by a known method (cf. the reference documents mentioned later in Examples etc.). The β-hydroxy-α-amino acid of the general formula [1] in which $R^2$ is methyl can be industrially most easily derived at low cost and is thus particularly preferred as the raw substrate material of the present invention.

Further, $Ar^1$ and $Ar^2$ each independently represent an aromatic ring group in the β-hydroxy-α-amino acid of the general formula [1]. Examples of the aromatic ring group as $Ar^1$ and $Ar^2$ are the same as $R^1$ in the β-hydroxy-α-amino acid of the general formula [1]. This aromatic ring group may have a substituent on any of carbon atoms thereof and may be an aromatic heterocyclic ring group containing a hetero atom. Among others, both of $Ar^1$ and $Ar^2$ are preferably phenyl. The β-hydroxy-α-amino acid of the general formula [1] in which both of $Ar^1$ and $Ar^2$ are phenyl can be derived from a corresponding amino group (—$NH_2$) industrially most easily at low cost with reference to Patent Document 1 or the like and is thus preferred as the raw substrate material of the present invention.

Further, * represents an asymmetric carbon in the β-hydroxy-α-amino acid of the general formula [1]. (When $R^1$ is a hydrogen atom, the β-position carbon atom is not an asymmetric carbon.) The inversion of the stereochemistry at the α-position proceeds with very high stereoselectivity through the reaction, whereas the stereochemistry at the β-position varies depending on the combination of the starting substrate and the organic base and the adopted reaction conditions. Each of the absolute configurations of the α- and β-position asymmetric carbons can be independently a R-configuration, a S-configuration or a mixture thereof. The absolute configuration of the α- and β-position asymmetric carbons of the β-hydroxy-α-amino acid are set as appropriate in accordance with the absolute configuration of the target α-fluoro-β-amino acid of the general formula [2] at the α- and β-positions.

In the case where the β-hydroxy-α-amino acid of the general formula [1] is in an optically active form, the optical purity of the β-hydroxy-α-amino acid is set depending on the uses of the target optically active pharmaceutical/agrichemical intermediate. It suffices that the β-hydroxy-α-amino acid has an enantiomer excess (ee) of 80% ee or higher. The enantiomer excess of the β-hydroxy-α-amino acid is generally preferably 90% ee or higher, more preferably 95% ee or higher. Further, it suffices that the diastereomer excess (de) of the β-hydroxy-α-amino acid, which is a measure of the relative configuration at the α- and β-positions, is 80% de or higher. The diastereomer excess of the β-hydroxy-α-amino acid is generally preferably 90% de or higher, more preferably 95% de or higher.

It suffices to use the sulfuryl fluoride ($SO_2F_2$) in an amount of 0.7 mol or more per 1 mol of the β-hydroxy-α-amino acid of the general formula [1]. The amount of the sulfuryl fluoride used is generally preferably in the range of 0.8 to 10 mol, more preferably 0.9 to 5 mol, per 1 mol of the β-hydroxy-α-amino acid of the general formula [1].

In the present invention, trifluoromethanesulfonyl fluoride ($CF_3SO_2F$) or perfluorobutanesulfonyl fluoride ($C_4F_9SO_2F$) can alternatively be used as the dehydroxyfluorination agent. There is however no particular advantage to using these reaction agents in view of their large-scale availability, fluorine atom economy and waste disposal (the sulfuryl fluoride can easily be processed to an inorganic salt waste such as fluorite ($CaF_2$) and calcium sulfate) etc.

In the present invention, the dehydroxyfluorination accompanied by 1,2-rearrangement is performed in the presence of the organic base. The organic base is preferably a tertiary amine having a carbon number of 8 to 12 and containing two or more alkyl groups of 3 or more carbon atoms, more preferably diisopropylethylamine. In the present specification, the term "tertiary amine" refers to an amine in which all of three hydrogen atoms of ammonia have been replaced by alkyl groups; and the term "carbon number" refers to a total number of carbons of the three alkyl groups.

Examples of the organic base are: trimethylamine (having a carbon number of 3 and containing no alkyl group of 3 or more carbon atoms); dimethylethylamine (having a carbon number of 4 and containing no alkyl group of 3 or more carbon atoms); diethylmethylamine (having a carbon number of 5 and containing no alkyl group of 3 or more carbon atoms); triethylamine (having a carbon number of 6 and containing no alkyl group of 3 or more carbon atoms); di-n-propylmethylamine (having a carbon number of 7 and containing two alkyl groups of 3 or more carbon atoms);

diisopropylethylamine (having a carbon number of 8 and containing two alkyl groups of 3 or more carbon atoms); tri-n-propylamine (having a carbon number of 9 and containing three alkyl groups of 3 or more carbon atoms); diisopropylisobutylamine (having a carbon number of 10 and containing three alkyl groups of 3 or more carbon atoms); dimethyl(n-nonyl)amine (having a carbon number of 11 and one alkyl group of 3 or more carbon atoms); tri-n-butylamine (having a carbon number of 12 and containing three alkyl groups of 3 or more carbon atoms); di-n-hexylmethylamine (having a carbon number of 13 and containing two alkyl groups of 3 or more carbon atoms); dimethyl(n-dodecyl)amine (having a carbon number of 14 and containing one alkyl group of 3 or more carbon atoms); tri-n-pentylamine (having a carbon number of 15 and containing three alkyl groups of 3 or more carbon atoms); pyridine; 2,3-lutidine; 2,4-lutidine; 2,6-lutidine; 3,4-lutidine; 3,5-lutidine; 2,4,6-collidine; 3,5,6-collidine; and the like.

Among others, the organic base of carbon number 8 or more is suitable for use in industrial production applications as it has high lipophilicity and can be easily recovered even by aqueous post treatment and recycled without reactivity deterioration.

It suffices to use the organic base in an amount of 0.7 mol or more per 1 mol of the β-hydroxy-α-amino acid of the general formula [1]. The amount of the organic base used is generally preferably in the range of 0.8 to 10 mol, more preferably 0.9 to 5 mol, per 1 mol of the β-hydroxy-α-amino acid of the general formula [1].

The dehydroxyfluorination accompanied by 1,2-rearrangement according to the present invention may be performed in the presence of "a salt or complex of an organic base and hydrogen fluoride" as another fluorine source. However, the reaction proceeds favorably even in the absence of such a salt or complex. There is thus no need to perform the reaction in the presence of the salt or complex.

Examples of the reaction solvent are: aliphatic hydrocarbon solvents such as n-hexane, cyclohexane and n-heptane; aromatic hydrocarbon solvents such as benzene, toluene, ethylbenzene, xylene and mesitylene; halogenated hydrocarbon solvents such as methylene chloride, chloroform and 1,2-dichloroethane; ether solvents such as diethyl ether, tetrahydrofuran, diisopropyl ether and tert-butyl methyl ether; ester solvents such as ethyl acetate and n-butyl acetate; amide solvents such as N,N-dimethylformamide, N,N-dimethylacetoamide, N-methyl-pyrrolidone and 1,3-dimethyl-2-imidazolidinone; nitrile solvents such as acetonitrile and propionitrile; dimethyl sulfoxide; and the like.

Among others, n-hexane, n-heptane, toluene, xylene, mesitylene, methylene chloride, tetrahydrofuran, diisopropyl ether, tert-butyl methyl ether, ethyl acetate, N,N-dimethylformamide, N,N-dimethylacetamide, acetonitrile, propionitrile and dimethyl sulfoxide are preferred. Particularly preferred are toluene, xylene, methylene chloride, tetrahydrofuran, diisopropyl ether, ethyl acetate, N,N-dimethylformamide and acetonitrile. These reaction solvents can be used alone or in combination thereof. Alternatively, the reaction may be performed in the absence of the reaction solvent in the present invention. It suffices to use the reaction solvent in an amount of 0.1 L (liter) or more per 1 mol of the β-hydroxy-α-amino acid of the general formula [1]. The amount of the reaction solvent used is generally preferably in the range of 0.2 to 10 L, more preferably 0.3 to 5 L, per 1 mol of the β-hydroxy-α-amino acid of the general formula [1].

It suffices that the temperature condition ranges from −100 to +100° C. The temperature condition is generally preferably in the range of −60 to +60° C., more preferably −50 to +50° C. In the case where the temperature condition is set to be higher than or equal to a boiling point (−49.7° C.) of the sulfuryl fluoride, the reaction can be conducted using a pressure-proof reaction vessel.

It suffices that the pressure condition ranges from atmospheric pressure to 2 MPa. The pressure condition is generally preferably in the range of atmospheric pressure to 1.5 MPa, more preferably atmospheric pressure to 1 MPa. It is thus preferable to conduct the reaction using a pressure-proof reaction vessel made of a stainless steel (SUS) material, a glass (glass-lined) material or the like. Further, it is efficient for large-scale charging of the sulfuryl fluoride into the pressure-proof reaction vessel to develop a negative pressure atmosphere in the reaction vessel, and then, introduce the sulfuryl fluoride in gas or liquid form under vacuum while increasing the pressure.

The reaction time is generally 72 hours or less. As the reaction time depends on the combination of the starting substrate and the organic base and the adopted reaction conditions, it is preferable to determine the time at which the starting substrate has almost disappeared as the end of the reaction while monitoring the progress of the reaction by any analytical means such as gas chromatography, thin-layer chromatography, liquid chromatography or nuclear magnetic resonance.

The target α-fluoro-β-amino acid of the general formula [2] can be obtained by ordinary post treatment of the reaction-terminated liquid. Further, the target product compound can be purified to a high chemical purity or high optical purity, as needed, by purification operation such as activated carbon treatment, distillation, recrystallization or column chromatography.

One effective technique of the post treatment is to dilute the reaction-terminated liquid with an organic solvent such as toluene, wash the diluted liquid with an aqueous solution of an inorganic base such as potassium carbonate, further wash the liquid with water, and then, subject the recovered organic phase to concentration (vacuum concentration and vacuum drying etc. as needed). By such post treatment, the target product can be obtained with sufficient quality as the substrate for the subsequent optional conversion reaction e.g. deprotection or the like.

As described above, in the present invention, the α-fluoro-β-amino acid of the general formula [2] is produced by reaction of the β-hydroxy-α-amino acid of the general formula [1] with sulfuryl fluoride ($SO_2F_2$) in the presence of the organic base. This process can suitably be applied for production of both of racemic and optically active forms.

Preferably, the optically active α-fluoro-β-amino acid of the general formula [4] is produced industrially easily with high position selectivity by reaction of the optically active β-hydroxy-α-amino acid of the general formula [3], corresponding to an optically active form of the β-hydroxy-α-amino acid of the general formula [1] in which: $R^1$ is hydrogen; both of $Ar^1$ and $Ar^2$ are phenyl; and $R^2$ is methyl ethyl or benzyl, with sulfuryl fluoride ($SO_2F_2$) in the presence of the tertiary amine having a carbon number of 8 to 12 and containing two or more alkyl groups of 3 or more carbon atoms.

More preferably, the optically active α-fluoro-β-amino acid of the formula [6] is produced industrially more easily with high position selectivity as a particularly important pharmaceutical intermediate by reaction of the optically active β-hydroxy-α-amino acid of the formula [5], corresponding to the optically active β-hydroxy-α-amino acid of the general formula [3] in which: $R^3$ is methyl; and the absolute configuration of the asymmetric carbon (*) at the α-position is a S-configuration, with sulfuryl fluoride (SO$_2$F$_2$) in the presence of diisopropylethylamine.

The present invention will be described in more detail below by way of the following examples. It should be noted that these examples are illustrative and are not intended to limit the present invention thereto.

In the following examples and comparative examples, the abbreviations for chemical groups are as follows: Bn=benzyl; Me=methyl; Ms=methanesulfonyl; Ac=acetyl; and n-Hep=n-heptyl.

Example 1

With reference to Patent Document 1, an optically active β-hydroxy-α-amino acid of the following formula:

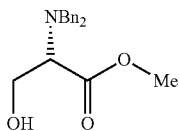

[Chem. 12]

was produced (α-position absolute configuration: S-configuration, optical purity: 97% ee or higher, gas chromatographic purity: 98.7%).

A pressure-proof reaction vessel of stainless steel (SUS) was charged with 1.00 g (3.34 mmol, 1.00 eq) of the optically active β-hydroxy-α-amino acid of the above formula, 5 mL of acetonitrile and 0.52 g (4.02 mmol, 1.20 eq) of diisopropylethylamine, followed by immersing the reaction vessel in a cooling bath of −78° C. and blowing 0.99 g (9.70 mmol, 2.90 eq) of sulfuryl fluoride (SO$_2$F$_2$) from a cylinder into the reaction vessel. The resulting liquid was stirred for one night at room temperature. The conversion rate of the reaction was determined to be 100% by gas chromatography of the reaction-terminated liquid.

The reaction-terminated liquid was diluted with 20 mL of toluene, washed with 20 mL of a saturated aqueous potassium carbonate solution and further washed with 20 mL of water. The recovered organic phase was vacuum concentrated and vacuum dried, thereby yielding 0.94 g of a mixture of an optically active α-fluoro-β-amino acid (α-F form) of the following formula:

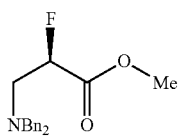

[Chem. 13]

and an optically active β-fluoro-α-amino acid (β-F form) of the following formula:

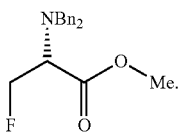

[Chem. 14]

The total yield of the α-F form and the β-F form was 93%. The gas chromatographic purity of the α-F form and the gas chromatographic purity of the β-F form were 91.8% and 1.4%, respectively (α-F form:β-F form=98.5:1.5). The optical purity was determined to be 98.1% ee by chiral liquid chromatography. There was almost no quaternary ammonium salt (trace amount or less) generated as by-product. The $^1$H-NMR and $^{19}$F-NMR analysis results of the α-F form are indicated below.

$^1$H-NMR [reference material: (CH$_3$)$_4$Si, deuterium solvent: CDCl$_3$] δ ppm/2.97 (ddd, 24.4 Hz, 14.6 Hz, 3.2 Hz, 1H), 3.04 (ddd, 24.4 Hz, 14.6 Hz, 6.0 Hz, 1H), 3.52 (d, 13.6 Hz, 2H), 3.69 (s, 3H), 3.83 (d, 13.6 Hz, 2H), 5.04 (ddd, 51.9 Hz, 6.0 Hz, 3.2 Hz, 1H), 7.20-7.40 (Ar—H, 10H).

$^{19}$F-NMR [reference material: C$_6$F$_6$, deuterium solvent: CDCl$_3$] δ ppm/−28.76 (dt, 51.9 Hz, 24.4 Hz, 1F).

As explained above, in Example 1, the reaction was performed with the use of the sulfuryl fluoride as the dehydroxyfluorination agent in the presence of the organic base (diisopropylethylamine). As a result, the α-F form was obtained with much higher position selectivity in Example 1 than that in Comparative Example 1 mentioned later. Further, the generation of the quaternary ammonium salt by-product was prevented effectively in Example 1 as compared to Example 2 using triethylamine as the organic base.

Example 2

A pressure-proof reaction vessel of stainless steel (SUS) was charged with 1.00 g (3.34 mmol, 1.00 eq, α-position absolute configuration: S-configuration, optical purity: 97% ee or higher, gas chromatographic purity: 98.7%) of an optically active βhydroxy-α-amino acid of the following formula:

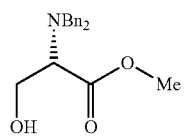

[Chem. 15]

10 mL of acetonitrile and 0.41 g (4.05 mmol, 1.21 eq) of triethylamine, followed by immersing the reaction vessel in a cooling bath of −78° C. and blowing 1.08 g (10.58 mmol, 3.17 eq) of sulfuryl fluoride (SO$_2$F$_2$) from a cylinder into the reaction vessel. The resulting liquid was stirred for one night at room temperature. The conversion rate of the reaction was determined to be 100% by gas chromatography of the reaction-terminated liquid.

The reaction-terminated liquid was diluted with 50 mL of toluene, washed with 50 mL of a saturated aqueous potassium carbonate solution and further washed with 50 mL of water. The recovered organic phase was vacuum concentrated and vacuum dried, thereby yielding 0.82 g of a mixture of an optically active α-fluoro-β-amino acid (α-F form) of the following formula:

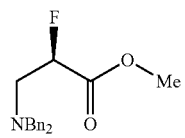

[Chem. 16]

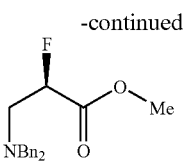

an optically active β-fluoro-α-amino acid (β-F form) of the following formula:

[Chem. 17]

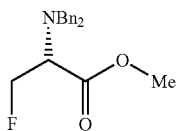

and a quaternary ammonium salt.

The total yield of the α-F form, the β-F form and the quaternary ammonium salt was 78%. The gas chromatographic purity of the α-F form and the gas chromatographic purity of the β-F form were 77.9% and 2.0%, respectively (α-F form:β-F form=97.5:2.5). (The gas chromatographic peak of the quaternary ammonium salt was not detected because of high boiling point of the quaternary ammonium salt.) The product ratio between the α-F form (including the β-F form) and the quaternary ammonium salt was determined to be 92:8 by $^{19}$F-NMR (more specifically, determined from the peak integral ratio between the fluorine atom of the fluorinated product and the fluorosulfuric anion). It is herein assumed that the substitution position of the triethylamine in the quaternary ammonium salt was mostly the α-position (for the reason that the methylene (—CH$_2$—) protons of —N$^+$(CH$_2$CH$_3$)$_3$ were detected as non-equivalent in the $^1$H-NMR analysis). The $^1$H-NMR and $^{19}$F-NMR analysis results of the α-F form were the same as those in Example 1.

Example 3

With reference to "Jikken Kagaku Koza 22, 4th Edition, Organic Synthesis IV: -Acid, Amino acid, Peptide-, (edited by The Chemical Society of Japan, published by MARUZEN Co. Ltd., Heisei 4, p. 214-228) as well as Patent Document 1, a β-hydroxy-α-amino acid (optically active form) of the following formula:

[Chem. 18]

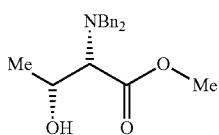

was produced (α-position absolute configuration: S-configuration, β-position absolute configuration: R-configuration, optical purity: 99% ee or higher, gas chromatographic purity: 95.3%).

A pressure-proof reaction vessel of stainless steel (SUS) was charged with 8.00 g (25.53 mmol, 1.00 eq) of the β-hydroxy-α-amino acid (optically active form) of the above formula, 26 mL of acetonitrile and 3.96 g (30.64 mmol, 1.20 eq) of diisopropylethylamine, followed by immersing the reaction vessel in a cooling bath of −78° C. and blowing 10.42 g (102.10 mmol, 4.00 eq) of sulfuryl fluoride (SO$_2$F$_2$) from a cylinder into the reaction vessel. The resulting liquid was stirred for 24 hours at 50° C. The conversion rate of the reaction was determined to be 94% by gas chromatography of the reaction-terminated liquid.

The reaction-terminated liquid was diluted with 100 mL of toluene, washed twice with 50 mL of a saturated aqueous potassium carbonate solution and further washed with 50 mL of water. The recovered organic phase was vacuum concentrated and vacuum dried, thereby yielding 8.21 g of a mixture of an α-fluoro-β-amino acid (optically active, α-F form) of the following formula:

[Chem. 19]

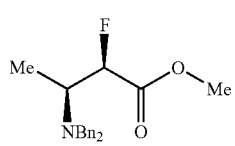

and a β-fluoro-α-amino acid (optically active, β-F form) of the following formula:

[Chem. 20]

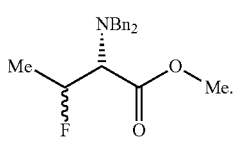

The total yield of the α-F form and the β-F form was quantitative (theoretical yield: 8.05 g). The gas chromatographic purity of the α-F form and the gas chromatographic purity of the β-F form were 61.8% and 25.5%, respectively (α-F form:β-F form=71:29). The β-F form was a mixture of syn- and anti-isomers; and the ratio between the syn- and anti-isomers was 69:31. The $^1$H-NMR and $^{19}$F-NMR analysis results of the α-F form are indicated below.

$^1$H-NMR [reference material: (CH$_3$)$_4$Si, deuterium solvent: CDCl$_3$] δ ppm/1.27 (d, 7.2 Hz, 3H), 3.29 (m, 1H), 3.33 (d, 13.6 Hz, 2H), 3.64 (s, 3H), 3.90 (d, 13.6 Hz, 2H), 4.84 (dd, 48.5 Hz, 3.6 Hz, 1H), 7.18-7.42 (Ar—H, 10H).

$^{19}$F-NMR [reference material: C$_6$F$_6$, deuterium solvent: CDCl$_3$] δ ppm/−39.59 (dd, 48.5 Hz, 30.5 Hz, 1F).

The $^1$H-NMR and $^{19}$F-NMR analysis results of the β-F form (syn configuration) are indicated below.

$^1$H-NMR [reference material: (CH$_3$)$_4$Si, deuterium solvent: CDCl$_3$] δ ppm/1.35 (dd, 24.4 Hz, 6.0 Hz, 3H), 3.37 (dd, 24.4 Hz, 6.0 Hz, 1H), 3.77 (d, 13.4 Hz, 2H), 3.79 (s, 3H), 4.06 (d, 13.4 Hz, 2H), 5.13 (d quintet, 48.9 Hz, 6.0 Hz, 1H), 7.18-7.42 (Ar—H, 10H).

$^{19}$F-NMR [reference material: C$_6$F$_6$, deuterium solvent: CDCl$_3$] δ ppm/−19.69 (d quintet, 48.9 Hz, 24.4 Hz, 1F).

In Example 3, the α-F form was obtained with much higher position selectivity than that in Comparative Example 2 mentioned later although the different β-hydroxy-α-amino acid from those in Examples 1 and 2 was used as the starting substrate as explained above.

Example 4

To a methanol solution (solvent amount: 8 mL) of 2.51 g (8.33 mmol, 1.00 eq) of an optically active α-fluoro-β-amino acid of the following formula:

[Chem. 21]

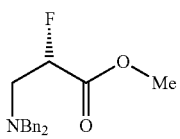

which had been prepared from D-serine in the same manner as above with reference to Example 1, 789 mg (0.185 mmol, 0.02 eq) of 5% palladium carbon (water content: 50%) and 1.00 g (16.7 mmol, 2.00 eq) of acetic acid were added. The resulting liquid was stirred for one night at room temperature under a hydrogen ($H_2$) pressure of 1.0 MPa. The conversion rate of the reaction was determined to be 100% by $^{19}$F-NMR of the reaction-terminated liquid.

The reaction-terminated liquid was subjected to Celite filtration. The filtrate was vacuum concentrated and vacuum dried, thereby yielding the optically active α-fluoro-β-amino acid in a deprotected form (acetate) of the following formula:

[Chem. 22]

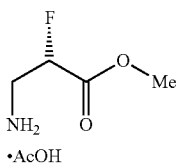

as an oily substance. To the whole of the acetate, 10.0 mL (10.0 mmol, 1.20 eq) of 1N hydrogen chloride/methanol was added. The resulting liquid was stirred for one night at room temperature.

The reaction-terminated liquid was vacuum concentrated and vacuum dried, thereby yielding 950 mg of a deprotected form (hydrochloride) of the optically active α-fluoro-β-amino acid as represented by the following formula:

[Chem. 23]

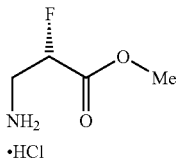

as a crystalline substance. The total product yield was 73%. The whole of the hydrochloride was washed by stirring at room temperature with the addition of 2 mL of isopropanol. The resulting liquid was subjected to filtration and vacuum drying. With this, 400 mg of a purified product was obtained. The product recovery rate was 42%. The $^1$H-NMR and $^{19}$F-NMR analysis results of the deprotected form (hydrochloride) of the optically active α-fluoro-β-amino acid are indicated below.

$^1$H-NMR [reference material: $(CH_3)_4Si$, deuterium solvent: $CD_3OD$] δ ppm/3.44 (m, 1H), 3.54 (m, 1H), 3.85 (s, 3H), 5.34 (m, 1H). The attributions of the amino group and hydrogen chloride proton were unidentified.

$^{19}$F-NMR [reference material: $C_6F_6$, deuterium solvent: $CD_3OD$] δ ppm/−34.31 (m, 1F).

In this way, the conversion from —$N(CH_2Ph)_2$ to —$NH_2$ was easily carried out.

Example 5

To 500 mg (1.66 mmol, 1.00 eq) of an optically active α-fluoro-β-amino acid of the following formula:

[Chem. 24]

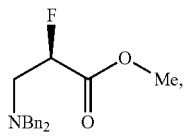

that had been produced with reference to Example 1, 6.00 g (57.6 mmol, 34.7 eq) of 35% hydrogen chloride and 2 mL of water were added. The resulting liquid was stirred for one night at room temperature. The conversion rate of the reaction was determined to be 100% by $^1$H-NMR of the reaction-terminated liquid.

The reaction-terminated liquid was vacuum concentrated and vacuum dried, thereby yielding 550 mg of a deprotected form (hydrochloride) of the optically active α-fluoro-β-amino acid as represented by the following formula:

[Chem. 25]

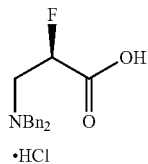

as a crystalline substance. The product yield was quantitative. The $^1$H-NMR and $^{19}$F-NMR analysis results of the deprotected form (hydrochloride) of the optically active α-fluoro-β-amino acid are indicated below.

$^1$H-NMR [reference material: $(CH_3)_4Si$, deuterium solvent: $CD_3OD$] δ ppm/3.63 (m, 1H), 3.74 (m, 1H), 4.51 (d, 13.4 Hz, 2H), 4.56 (d, 13.4 Hz, 2H), 5.61 (m, 1H), 7.46-7.60 (m, 10H). The attributions of the carboxyl group and hydrogen chloride proton were unidentified.

$^{19}$F-NMR [reference material: $C_6F_6$, deuterium solvent: $CD_3OD$] δ ppm/−26.26 (m, 1F).

The conversion from —$CO_2Me$ to —$CO_2H$ was easily carried out in this way.

Example 6

To a tetrahydrofuran solution (solvent amount: 10 mL) of 3.01 g (9.99 mmol, 1.00 eq) of an optically active α-fluoro-β-amino acid of the following formula:

[Chem. 26]

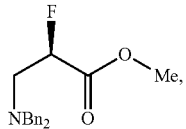

that had been produced with reference to Example, 1380 mg (10.0 mmol, 1.00 eq) of lithium aluminum hydride ($LiAlH_4$) was added under ice cooling. The resulting liquid was stirred for 2 hours at the same temperature as above. The conversion rate of the reaction was determined to be 100% by $^1$H-NMR and $^{19}$F-NMR of the reaction-terminated liquid.

To the reaction-terminated liquid, 5 mL of water was added. The thus-obtained liquid was stirred for 30 minutes at 45° C. and subjected to Celite filtration. The residue was washed with 10 mL of ethyl acetate. The filtrate was vacuum concentrated and vacuum dried, thereby yielding 3.10 g of an optically active 2-fluoro-3-aminopropanol of the following formula:

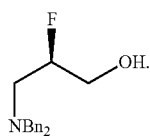

[Chem. 27]

The product yield was quantitative. The gas chromatographic purity was 96.4%. The $^1$H-NMR and $^{19}$F-NMR analysis results of the optically active 2-fluoro-3-aminopropanol are indicated below.

$^1$H-NMR [reference material: $(CH_3)_4Si$, deuterium solvent: $CDCl_3$] δ ppm/2.71-2.88 (m, 2H), 2.94 (br, 1H), 3.60 (d, 13.2 Hz, 2H), 3.65 (m, 2H), 3.72 (d, 13.2 Hz, 2H), 4.63 (m, 1H), 7.10-7.50 (Ar—H, 10H).

$^{19}$F-NMR [reference material: $C_6F_6$, deuterium solvent: $CDCl_3$] δ ppm/−29.61 (dquin, 44.2 Hz, 21.4 Hz, 1F).

In this way, the conversion from the optically active α-fluoro-β-amino acid to the optically active 2-fluoro-3-aminopropanol was easily carried out.

Example 7

With reference to Patent Document 1, an optically active β-hydroxy-α-amino acid of the following formula:

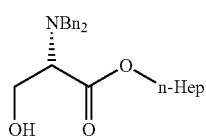

[Chem. 28]

was produced. (The reaction rate of the n-heptylesterification was lower than that of the methylesterification so that the n-heptylesterification needed stirring for 4 days at 50° C. The n-heptyl ester was converted into a N,N-dibenzyl derivative in the same manner as the methyl ester. The total yield from L-serine was quantitative.) The $^1$H-NMR analysis results of the optically active β-hydroxy-α-amino acid are indicated below.

$^1$H-NMR [reference material: $(CH_3)_4Si$, deuterium solvent: $CDCl_3$] δ ppm/0.91 (t, 7.0 Hz, 3H), 1.20-1.50 (m, 8H), 1.72 (quin, 7.4 Hz, 2H), 2.53 (dd, 7.4 Hz, 4.2 Hz, 1H), 3.55 (t, 7.6 Hz, 1H), 3.69 (d, 13.4 Hz, 2H), 3.76 (m, 2H), 3.92 (d, 13.4 Hz, 2H), 4.20 (m, 2H), 7.12-7.44 (Ar—H, 10H).

A pressure-proof reaction vessel of stainless steel (SUS) was charged with 2.00 g (5.21 mmol, 1.00 eq) of the optically active β-hydroxy-α-amino acid of the above formula, 5 mL of acetonitrile and 0.81 g (6.27 mmol, 1.20 eq) of diisopropylethylamine, followed by immersing the reaction vessel in a cooling bath of −78° C. and blowing 1.06 g (10.4 mmol, 2.00 eq) of sulfuryl fluoride ($SO_2F_2$) from a cylinder into the reaction vessel. The resulting liquid was stirred for one night at room temperature. The conversion rate of the reaction was determined to be 100% by gas chromatography of the reaction-terminated liquid.

The reaction-terminated liquid was diluted with 50 mL of toluene, washed with 50 mL of a saturated aqueous potassium carbonate solution and further washed with 50 mL of water. The recovered organic phase was vacuum concentrated and vacuum dried, thereby yielding 1.82 g of a mixture of an optically active α-fluoro-β-amino acid (α-F form) of the following formula:

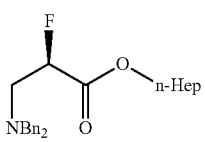

[Chem. 29]

and an optically active βfluoro-α-amino acid (β-F form) of the following formula:

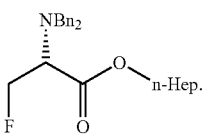

[Chem. 30]

The total yield of the α-F form and the β-F form was 91%. The gas chromatographic purity of the α-F form and the gas chromatographic purity of the β-F form were 94.8% and 3.4%, respectively (α-F form:β-F form=96.5:3.5) (as analyzed after converting to an methyl ester by treatment with hydrogen chloride/methanol). The optical purity was determined to be 98.3% ee by chiral liquid chromatography (as analyzed after converting to a methyl ester by treatment with chydrogen chloride/methanol). There was almost no (a trace amount or less) quaternary ammonium salt generated as a by-product. The $^1$H-NMR and $^{19}$F-NMR analysis results of the α-F form are indicated below.

$^1$H-NMR [reference material: $(CH_3)_4Si$, deuterium solvent: $CDCl_3$] δ ppm/0.89 (t, 6.8 Hz, 3H), 1.27 (m, 8H), 1.56 (m, 2H), 2.99 (m, 1H), 3.04 (m, 1H), 3.57 (d, 13.6 Hz, 2H), 3.82 (d, 13.6 Hz, 2H), 4.04 (m, 1H), 4.16 (m, 1H), 5.05 (m, 1H), 7.10-7.50 (Ar—H, 10H).

$^{19}$F-NMR [reference material: $C_6F_6$, deuterium solvent: $CDCl_3$] δ ppm/−28.48 (dt, 50.8 Hz, 25.1 Hz, 1F).

As explained above, the optically active βhydroxy-α-amino acid even in which the ester moiety was n-heptyl ester underwent a desired reaction favorably.

Comparative Example 1

Follow-Up Experiment of Patent Document 1

To 10 mL of toluene, 1.00 g (3.34 mmol, 1.00 eq, α-position absolute configuration: S-configuration, optical purity: 97% ee or higher, gas chromatographic purity: 94.3%) of an optically active βhydroxy-α-amino acid of the following formula:

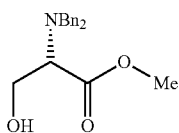

[Chem. 31]

and 0.37 g (3.66 mmol, 1.10 eq) of triethylamine was added. The resulting liquid was mixed with 0.42 g (3.67 mmol, 1.10 eq) of methanesulfonyl chloride while immersing the reaction vessel in an ice bath, and then, was stirred for 35 minutes at 0° C. The conversion rate of the reaction was determined to be 100% by gas chromatography of the reaction-terminated liquid.

The reaction-terminated liquid was diluted with 50 mL of toluene, washed with 50 mL of a 0.7M aqueous sodium carbonate solution, washed with 50 mL of water and further washed with 50 mL of a saturated sodium chloride solution. The recovered organic phase was vacuum concentrated and vacuum dried, thereby yielding 1.34 g of a methanesulfonate derivative of the following formula:

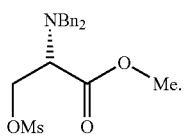

[Chem. 32]

The product yield was quantitative (theoretical yield: 1.26 g). The gas chromatographic purity was 93.2%. The $^1$H-NMR analysis results are indicated below.

$^1$H-NMR [reference material: $(CH_3)_4Si$, deuterium solvent: $CDCl_3$] δ ppm/2.90 (s, 3H), 3.65 (d, 13.8 Hz, 2H), 3.74 (t, 6.6 Hz, 1H), 3.83 (s, 3H), 3.86 (d, 13.8 Hz, 2H), 4.33 (dd, 10.0 Hz, 6.6 Hz, 1H), 4.48 (dd, 10.0 Hz, 6.6 Hz, 1H), 7.12-7.44 (Ar—H, 10H).

The whole (3.34 mmol, 1.00 eq) of the methanesulfonate derivative of the above formula and 0.54 g (3.35 mmol, 1.00 eq) of triethylamine tris(hydrogen fluoride) complex were added to 20 mL of toluene. The resulting liquid was stirred for 2 hours and 30 minutes at 90° C. The conversion rate of the reaction was determined to be 89% by gas chromatography of the reaction-terminated liquid.

The reaction-terminated liquid was diluted with 30 mL of toluene, washed by adding 30 mL of water and 20 mL of 28% aqueous ammonia (aqueous phase: pH10) and further washed twice with 30 mL of water. The recovered organic phase was vacuum concentrated and vacuum dried, thereby yielding 0.94 g of a mixture of an optically active α-fluoro-β-amino acid (α-F form) of the following formula:

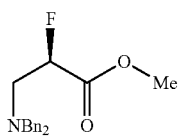

[Chem. 33]

and an optically active βfluoro-α-amino acid (β-F form) of the following formula:

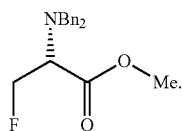

[Chem. 34]

The total yield of the α-F form and the β-F form was 93%. The gas chromatographic purity of the α-F form and the gas chromatographic purity of the β-F form were 81.7% and 7.1%, respectively (α-F form:β-F form=92.0:8.0). The $^1$H-NMR and $^{19}$F-NMR analysis results of the α-F form were the same as those in Example 1.

Comparative Example 2/DAST

To 20 mL of tetrahydrofuran, 3.00 g (9.57 mmol, 1.00 eq, α-position absolute configuration: S-configuration, β-position absolute configuration: R-configuration, optical purity: 99% ee or higher, gas chromatographic purity: 95.3%) of a β-hydroxy-α-amino acid (optically active form) of the following formula:

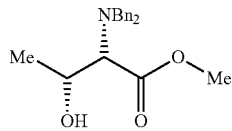

[Chem. 35]

was added. The resulting liquid was mixed with 1.95 g (12.10 mmol, 1.26 eq) of DAST $((CH_3CH_2)_2NSF_3)$ while immersing the reaction vessel in an ice bath, and then, was stirred at room temperature for 30 minutes. The conversion rate of the reaction was determined to be 100% by $^1$H-NMR of the reaction-terminated liquid.

The reaction-terminated liquid was diluted with 50 mL of ethyl acetate, washed with 20 mL of a saturated aqueous potassium carbonate solution and further washed with 20 mL of water. The recovered organic phase was vacuum concentrated and vacuum dried, thereby yielding 2.79 g of a mixture of an α-fluoro-β-amino acid (optically active, α-F form) of the following formula:

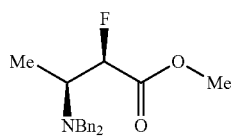

[Chem. 36]

and a β-fluoro-α-amino acid (optically active, β-F form) of the following formula:

[Chem. 37]

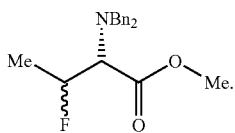

The total yield of the α-F form and the β-F form was 92%. The gas chromatographic purity of the α-F form and the gas chromatographic purity of the β-F form were 55.3% and 43.8%, respectively (α-F form:β-F form=56:44). Although the β-F form was a mixture of syn- and anti-isomers, most of the β-F form was the syn-isomer (the anti-isomer was in a trace amount). The $^1$H-NMR and $^{19}$F-NMR analysis results of the α-F form and the β-F form (syn-isomer) were the same as those in Example 3.

The invention claimed is:

1. A process for producing an α-fluoro-β-amino acid of the general formula [2], comprising: reacting a β-hydroxy-α-amino acid of the general formula [1] with sulfuryl fluoride ($SO_2F_2$) in the presence of an organic base

[Chem. 38]

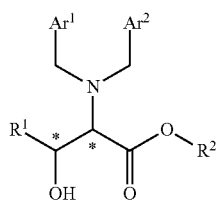

[1]

[Chem. 39]

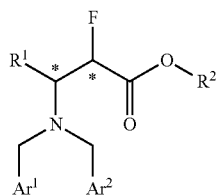

[2]

where $R^1$ represents a hydrogen atom, an alkyl group or an aromatic ring group; $R^2$ represents an alkyl group; $Ar^1$ and $Ar^2$ each independently represent an aromatic ring group; * represents an asymmetric carbon (when $R^1$ is a hydrogen atom, the β-position carbon atom is not an asymmetric carbon); the alkyl group or aromatic ring group represented by $R^1$, $R^2$, $Ar^1$ and $Ar^2$ may have a substituent on any of carbon atoms thereof; and the aromatic ring group may be an aromatic heterocyclic group containing a hetero atom.

2. A process for producing an optically active α-fluoro-β-amino acid of the general formula [4], comprising: reacting an optically active β-hydroxy-α-amino acid of the general formula [3] with sulfuryl fluoride ($SO_2F_2$) in the presence of a tertiary amine having a carbon number of 8 to 12 and containing two or more alkyl groups of 3 or more carbon atoms

[Chem. 40]

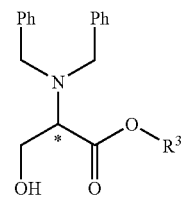

[3]

[Chem. 41]

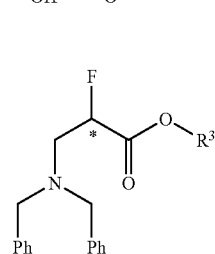

[4]

where $R^3$ represents a methyl group, an ethyl group or a benzyl group; Ph represents a phenyl group; and * represents an asymmetric carbon.

3. A process for producing an optically active α-fluoro-β-amino acid of the formula [6], comprising: reacting an optically active β-hydroxy-α-amino acid of the formula [5] with sulfuryl fluoride ($SO_2F_2$) in the presence of diisopropylethylamine

[Chem. 42]

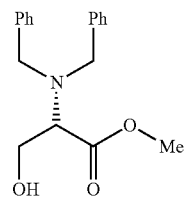

[5]

[Chem. 43]

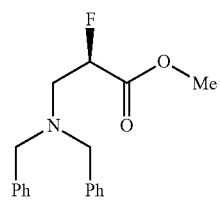

[6]

where Me represents a methyl group; and Ph represents a phenyl group.

* * * * *